(12) United States Patent
Kawabe et al.

(10) Patent No.: US 7,662,366 B2
(45) Date of Patent: Feb. 16, 2010

(54) METHOD OF PREVENTING β CELL DISRUPTION IN PANCREATIC LANGERHANS' ISLETS

(75) Inventors: Yoshiki Kawabe, Gotenba (JP); Yuichiro Adachi, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 18 days.

(21) Appl. No.: 10/553,672

(22) PCT Filed: Apr. 15, 2004

(86) PCT No.: PCT/JP2004/005397

§ 371 (c)(1), (2), (4) Date: Oct. 17, 2005

(87) PCT Pub. No.: WO2004/091661

PCT Pub. Date: Oct. 28, 2004

(65) Prior Publication Data

US 2007/0098680 A1 May 3, 2007

(30) Foreign Application Priority Data

Apr. 15, 2003 (JP) .............................. 2003-110561

(51) Int. Cl.
*A61K 45/00* (2006.01)
*A61K 38/19* (2006.01)

(52) U.S. Cl. .................... 424/85.1; 514/12; 530/399

(58) Field of Classification Search .................. None
See application file for complete search history.

(56) References Cited

U.S. PATENT DOCUMENTS

| | | | | |
|---|---|---|---|---|
| 5,629,286 A | * | 5/1997 | Brewitt | 514/2 |
| 6,001,647 A | * | 12/1999 | Peck et al. | 435/325 |
| 6,232,288 B1 | * | 5/2001 | Kojima | 514/2 |
| 6,303,146 B1 | * | 10/2001 | Bonhomme et al. | 424/465 |
| 6,610,535 B1 | * | 8/2003 | Lu et al. | 435/325 |
| 6,759,039 B2 | * | 7/2004 | Tsang et al. | 424/93.7 |
| 2004/0136969 A1 | * | 7/2004 | Hussain | 424/93.7 |

FOREIGN PATENT DOCUMENTS

| JP | 2001 233784 | * | 8/2001 |
|---|---|---|---|
| WO | WO 02/50263 | * | 12/2000 |
| WO | WO/2004/030628 | * | 10/2003 |

OTHER PUBLICATIONS

Canturk et al., Effects of rG-CSF on neutrophil functions and bone marrow parameters in diabetic rats. Endocrine Research.(abstract) 25, 381-395, 1999.*
Sato et al., Effect of G-CSF on generation of oxygen-derived free radicals and myeloperoxidase activity in neutrophils from poorly controlled NIDDM patients. Diabetes, 46, 133-137, 1997.*
Krakowski et al. Granulocyte macrophage-colony stimulating factor (GM-CSF)recruits immune cells to the pancreas and delays STZ-induced diabetes. J Pathol. 16, 103-112, 2002.*
Lukic et al., Effector Mechanisms In Low-Dose Streptozotocin-Induced Diabetes, Develop. Immunol., 6, 119-128, 1998.*
Dalhoff et al., Inhibition of neotrophil apoptosis and modulation of the nflammatory response by granulocyte colony-stimulating factor in healthy and ethanol-treated human volunteers. J. Infect. Diseases, 178, 891-895, 1998.*
Soria et al. Insulin-Secreting Cells Derived From Embryonic Stem Cells Normalize Glycemia in Streptozotocin-Induced Diabetic Mice. Diabetes, 49, 1-6, 2000.*
Takano et al., Pleiotropic Effects of Cytokines on Acute Myocardial Infarction: G-CSF asA Novel Therapy for Acute Myocardial Infarction. Curr. Pharm. Drugs, 9, 1121-1127, 2003.*
Maedler et al. Glucose-induced βcell production of IL-1βcontributes to glucotoxicity in human pancreatic islets. J. Clinical Investigation, 10, 851-860, 2002.*
Yamaoka T., Regeneration therapy of pancreatic beta cells: towards a cure for diabetes? Biochem. Biophys. Res. Commun. 296, 1039-1043, 2002.*
Paris et al., Pancreatic β-Cell Neogenesis Revisited. Experim. Diab. Res. 5, 111-121, 2004.*
Bernard-Kargar et al., Endocrine Pancreas Plasticity Under Physiologicaland Pathological Conditions. Diabetes, 50 (suppl. 1) S30-S35, 2001.*
Andreas Lechner et al., 'Stem/progenitor cells derived from adult tissues: potential for the treatment of diabetes mellitus, *Am. J. Physiol. Endocrinol. Metab.*, 2003, 284(2), 259-266.

* cited by examiner

*Primary Examiner*—Lorraine Spector
*Assistant Examiner*—Elly-Gerald Stoica
(74) *Attorney, Agent, or Firm*—Browdy and Neimark, PLLC

(57) ABSTRACT

The object of the present invention is to provide a method for treating diabetes which is simple, safe and effective when compared to conventional diabetes treatment. The administration of one or more stem cell-recruiting factors allows a simple and safe repair of disrupted β-cells in pancreatic Langerhans' islets. Thus, the therapeutic agent of the present invention which comprises one or more stem cell-recruiting factors as active ingredients is useful for diabetes treatment. Examples of such a stem cell-recruiting factor include colony-stimulating factors such as G-CSF.

2 Claims, 2 Drawing Sheets

SEQUENCE LISTING

<160> NUMBER OF SEQ ID NOS: 1

<210> SEQ ID NO 1
<211> LENGTH: 174
<212> TYPE: PRT
<213> ORGANISM: Human

<400> SEQUENCE: 1

```
Thr Pro Leu Gly Pro Ala Ser Ser Leu Pro Gln Ser Phe Leu Leu Lys
1               5                   10                  15
Cys Leu Glu Gln Val Arg Lys Ile Gln Gly Asp Gly Ala Ala Leu Gln
            20                  25                  30
Glu Lys Leu Cys Ala Thr Tyr Lys Leu Cys His Pro Glu Glu Leu Val
        35                  40                  45
Leu Leu Gly His Ser Leu Gly Ile Pro Trp Ala Pro Leu Ser Ser Cys
    50                  55                  60
Pro Ser Gln Ala Leu Gln Leu Ala Gly Cys Leu Ser Gln Leu His Ser
65                  70                  75                  80
Gly Leu Phe Leu Tyr Gln Gly Leu Leu Gln Ala Leu Glu Gly Ile Ser
                85                  90                  95
Pro Glu Leu Gly Pro Thr Leu Asp Thr Leu Gln Leu Asp Val Ala Asp
            100                 105                 110
Phe Ala Thr Thr Ile Trp Gln Gln Met Glu Glu Leu Gly Met Ala Pro
        115                 120                 125
Ala Leu Gln Pro Thr Gln Gly Ala Met Pro Ala Phe Ala Ser Ala Phe
    130                 135                 140
Gln Arg Arg Ala Gly Gly Val Leu Val Ala Ser His Leu Gln Ser Phe
145                 150                 155                 160
Leu Glu Val Ser Tyr Arg Val Leu Arg His Leu Ala Gln Pro
                165                 170
```

METHOD OF PREVENTING β CELL DISRUPTION IN PANCREATIC LANGERHANS' ISLETS

TECHNICAL FIELD

The present invention relates to an agent for treating diabetes, an agent for regenerating β-cells in pancreatic Langerhans' islets and an agent for preventing β-cell disruption in pancreatic Langerhans' islets, each agent comprising a stem cell-recruiting factor or factors as an active ingredient(s). The present invention also relates to a method for producing pancreatic Langerhans β-cells, which comprises administering a stem cell-recruiting factor or factors.

BACKGROUND ART

Diabetes is a group of diseases characterized by chronic hyperglycemia induced by a lack of insulin action, along with various characteristic metabolic abnormalities. Prolonged metabolic abnormalities tend to cause inherent complications and also promote arteriosclerosis. Diabetes can be broadly divided into type I and type II. Type I is characterized by β-cell disruption in pancreatic Langerhans' islets as its onset mechanism, while reductions in both insulin secretion and insulin sensitivity (insulin resistance) are involved in the onset of type II. Pancreatic Langerhans β-cells are one of four secretory cells (α-cells, β-cells, δ-cells and PP cells) constituting Langerhans' islets (pancreatic islets) and secrete insulin.

It is reported that there are about two million diabetic patients in Japan. For treatment of diabetes, diet therapy, exercise therapy and drug therapy including insulin therapy have been used. These therapies enable diabetes to be controlled to some extent, but each therapy still has problems.

Namely, diet therapy prescribes calorie restriction as well as protein restriction for patients whose condition is further complicated by nephropathy, although this therapy should be followed every day over a long period of time. Moreover, as diet therapy is mostly controlled by the patients themselves or their family members, there is a problem that many patients give up continuing the therapy.

Exercise therapy is also important in that it must become an everyday activity of the patient. However, when attention is directed exclusively to exercise therapy while ignoring diet therapy, exercise therapy will have the opposite effect on diabetes control to what was intended, as a result of increased appetite.

In drug therapy, insulin is used for treatment of a part of type I and type II diabetes. However, although insulin therapy has a dramatic effect on the reduction of blood glucose, the therapy requires daily administration of self-injections and is merely a symptomatic treatment. On the other hand, oral hypoglycemic agents include sulfonylurea (SU) drugs and biguanide drugs. However, these drugs have problems such as β-cell exhaustion induced by the random use of SU drugs and side effects of lactic acidosis caused by biguanide drugs. Under present circumstances, all of these drugs are used for symptomatic treatment and there is no therapeutic agent for a radical treatment. Thiazolidine derivatives recently developed as agents for ameliorating insulin resistance also cause many side effects and tend to produce results clearly polarized between effective and non-effective.

At present, based on the concept of radical treatment, attempts have been made to develop β-cell transplantation using embryonic stem cells or differentiation-inducing therapy involving expression of a specific gene in β-cell progenitors within pancreatic tissues, and these attempts have reached the preclinical stage.

Recent studies have indicated that stem cells present in the bone marrow are pluripotent and differentiated into blood vessels or cardiac muscle cells, etc. Likewise, it has been found that bone marrow-derived cells are also differentiated into endodermal tissues such as intestinal cells or pancreatic β-cells and are involved in the regeneration of these tissues.

Human G-CSF is a hematopoietic factor found as a differentiation-inducing factor for hematopoietic stem cells of the granulocytic lineage and is clinically used as a therapeutic agent for neutropenia following bone marrow transplantation or cancer chemotherapy because it promotes in vivo hematopoiesis of neutrophils. In addition to this action, human G-CSF acts on stem cells to stimulate their differentiation and proliferation, and also recruits stem cells from the bone marrow into the peripheral blood. Based on the latter action, in fact, transplantation of the peripheral blood hematopoietic stem cells recruited by human G-CSF, i.e., peripheral blood stem cell transplantation is performed in a clinical setting, with the aim of accelerating hematopoietic recovery in cancer patients after intensive chemotherapy.

DISCLOSURE OF THE INVENTION

The object of the present invention is to provide a method for treating diabetes which is simple, safe and effective when compared to conventional diabetes treatment.

The inventors of the present invention have examined the repairing effects on disrupted organs or the like using stem cell-recruiting action of G-CSF. As a result, the inventors have found that disrupted pancreatic Langerhans β-cells can be repaired by G-CSF administration and hence G-CSF is useful as a therapeutic agent for diabetes. This finding led to the completion of the present invention.

Namely, the present invention provides an agent for treating diabetes, which comprises a stem cell-recruiting factor or factors as an active ingredient(s).

The present invention also provides an agent for regenerating β-cells in pancreatic Langerhans' islets, which comprises a stem cell-recruiting factor or factors as an active ingredient(s).

The present invention further provides an agent for preventing β-cell disruption in pancreatic Langerhans' islets, which comprises a stem cell-recruiting factor or factors as an active ingredient(s).

The present invention further provides a method for producing pancreatic Langerhans β-cells, which comprises the steps of: (a) collecting stem cells after administering a stem cell-recruiting factor or factors; and (b) differentiating the collected stem cells into pancreatic Langerhans β-cells.

BEST MODE FOR CARRYING OUT THE INVENTION

Figure 1:
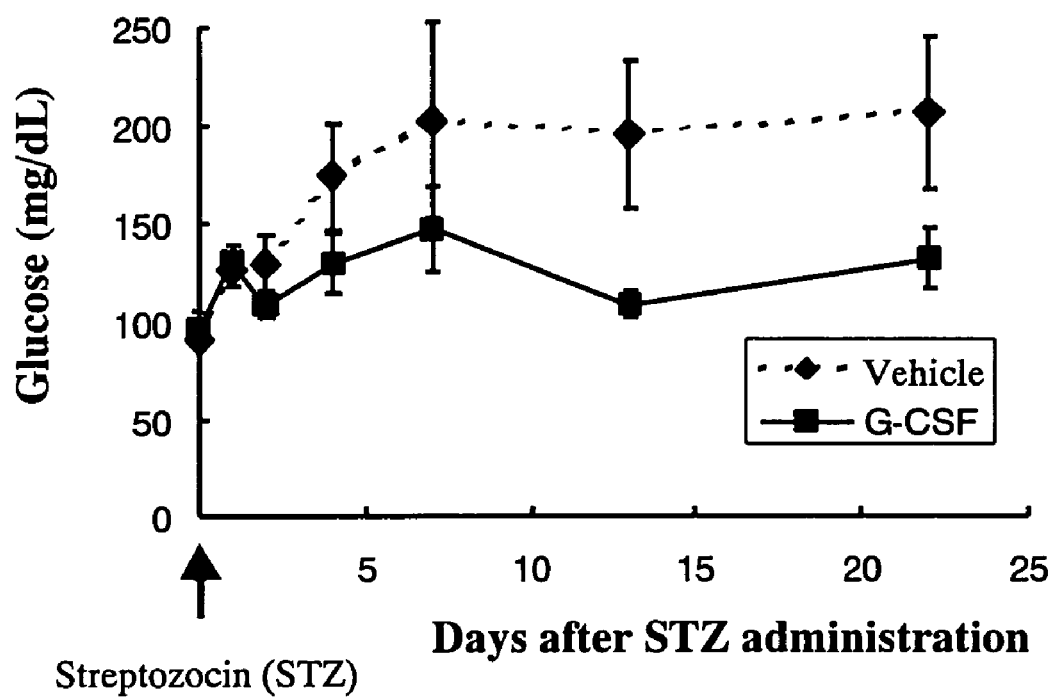
FIG. 1 is a graph showing the influence of G-CSF administration on blood glucose concentrations.

The agent for treating diabetes of the present invention comprises a stem cell-recruiting factor or factors as an active ingredient(s).

The agent for treating diabetes of the present invention may be targeted at any type of diabetes, either type I or type II diabetes, preferably type II diabetes.

Examples of stem cells include embryonic stem cells (ES cells), undifferentiated cells in the pancreatic duct, hepatic stem cells in the liver and intestinal stem cells.

Any factor may be used as a stem cell-recruiting factor as long as it can perform the action of recruiting stem cells. Specific examples of a stem cell-recruiting factor include, for example, colony-stimulating factors (e.g., granulocyte-macrophage colony-stimulating factor (GM-CSF), granulocyte colony-stimulating factor (G-CSF)), stem cell factor (SCF), and erythropoietin (EPO). Preferred are colony-stimulating factors and more preferred is granulocyte colony-stimulating factor (G-CSF).

G-CSF suitable for use as an active ingredient in the agent for treating diabetes of the present invention is not limited in any way, but it is preferable that the G-CSF is highly purified. Specific examples include mammalian G-CSF, particularly those having substantially the same biological activities as human G-CSF. G-CSF used herein may be of any origin, including those naturally occurring and those produced recombinantly, with recombinantly produced G-CSF being preferred. Such recombinantly produced G-CSF may have the same amino acid sequence as naturally-occurring G-CSF (see SEQ ID NO: 1) or may comprise deletion, substitution and/or addition of one or more amino acid residues in the amino acid sequence as long as it retains the same biological activities as naturally-occurring G-CSF. Amino acid deletions, substitutions or additions may be accomplished in a manner known to those skilled in the art. For example, those skilled in the art will be able to use site-specific mutagenesis (Gotoh, T. et al. (1995) Gene 152, 271-275; Zoller, M. J. and Smith, M. (1983) Methods Enzymol. 100, 468-500; Kramer, W. et al. (1984) Nucleic Acids Res. 12, 9441-9456; Kramer, W. and Fritz, H. J. (1987) Methods Enzymol. 154, 350-367; Kunkel, T. A. (1985) Proc. Natl. Acad. Sci. USA. 82, 488-492; Kunkel (1988) Methods Enzymol. 85, 2763-2766) or other techniques to introduce appropriate mutations into the amino acid sequence of G-CSF, thereby preparing a polypeptide functionally equivalent to G-CSF. Likewise, amino acid mutations may also occur in the natural world. In general, amino acid residues to be substituted are preferably replaced with other amino acids in such a manner as to conserve the nature of amino acid side chains. With regard to the nature of amino acid side chains, examples include hydrophobic amino acids (A, I, L, M, F, P, W, Y, V), hydrophilic amino acids (R, D, N, C, E, Q, G, H, K, S, T), amino acids having an aliphatic side chain (G, A, V, L, I, P), amino acids having a hydroxy-containing side chain (S, T, Y), amino acids having a sulfur-containing side chain (C, M), amino acids having a carboxylic acid- or amide-containing side chain (D, N, E, Q), amino acids having a base-containing side chain (R, K, H), and amino acids having an aromatic-containing side chain (H, F, Y, W) (capital letters in parentheses refer to the corresponding amino acids in single-letter notation). It is already known that a polypeptide having an amino acid sequence modified from another amino acid sequence by deletion and/or addition of one or more amino acid residues and/or by their substitution with other amino acids retains the same biological activities as the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; Dalbadie-McFarland, G. et al., Proc. Natl. Acad. Sci. USA (1982) 79, 6409-6413).

It is also possible to use fusion proteins between G-CSF and other proteins. To prepare a fusion polypeptide, for example, DNA encoding G-CSF and DNA encoding another protein may be ligated together in-frame, introduced into an expression vector and then expressed in a host. Other proteins to be fused herein with G-CSF are not limited in any way.

Moreover, it is also possible to use chemically modified G-CSF. Examples of chemically modified G-CSF include those modified by structural alteration, addition and/or deletion of sugar chains, as well as those conjugated with a compound such as an inorganic or organic compound (e.g., polyethylene glycol, vitamin B12).

G-CSF used in the present invention may be prepared in any manner, for example, by culturing human tumor cell lines or human G-CSF-producing hybridoma cell lines or by genetically engineered production in *E. coli* cells, yeast cells, Chinese hamster ovary (CHO) cells, C127 cells, COS cells, myeloma cells, BHK cells, insect cells, etc. G-CSF thus prepared is extracted, isolated and purified in various manners before use. G-CSF used in the present invention is preferably a genetically engineered one, more preferably G-CSF produced in mammalian cells (particularly CHO cells) (e.g., JP 1-44200 B, JP 2-5395 B, JP 62-129298 A, JP 62-132899 A, JP 62-236488 A, JP 64-85098 A).

If necessary, depending on the administration mode and the dosage form, the agent for treating diabetes of the present invention may be supplemented as appropriate with a suspending agent, a solubilizing agent, a stabilizing agent, an isotonizing agent, a preservative, an anti-adsorption agent, a surfactant, a diluent, an excipient, a pH adjustor, a soothing agent, a buffer, a sulfur-containing reducing agent, an antioxidant or the like.

Examples of a suspending agent include methylcellulose, Polysorbate 80, hydroxyethylcellulose, gum arabic, powdered tragacanth, carboxymethylcellulose sodium, and polyoxyethylenesorbitan monolaurate.

Examples of a solubilizing agent include polyoxyethylene hydrogenated castor oil, Polysorbate 80, nicotinamide, polyoxyethylenesorbitan monolaurate, Magrogol, and an ethyl ester of castor oil fatty acid.

Examples of a stabilizing agent include Dextran 40, methylcellulose, gelatin, sodium sulfite, and sodium metasulfite.

Examples of an isotonizing agent include D-mannitol and sorbitol.

Examples of a preservative include methyl paraoxybenzoate, ethyl paraoxybenzoate, sorbic acid, phenol, cresol, and chlorocresol.

Examples of an anti-adsorption agent include human serum albumin, lecithin, dextran, ethylene oxide-propylene oxide copolymers, hydroxypropylcellulose, methylcellulose, polyoxyethylene hydrogenated castor oil, and polyethylene glycol.

Examples of a sulfur-containing reducing agent include those having a sulfhydryl group such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and a $C_1$-$C_7$ thioalkanoic acid.

Examples of an antioxidant include erythorbic acid, dibutylhydroxytoluene, butylhydroxyanisole, α-tocopherol, tocopherol acetate, L-ascorbic acid and a salt thereof, L-ascorbyl palmitate, L-ascorbyl stearate, sodium bisulfite, sodium sulfite, triamyl gallate and propyl gallate, as well as chelating agents such as ethylenediaminetetraacetic acid disodium salt (EDTA), sodium pyrophosphate and sodium metaphosphate.

Furthermore, the agent for treating diabetes of the present invention may comprise other commonly used ingredients, e.g., inorganic salts such as sodium chloride, potassium chloride, calcium chloride, sodium phosphate, potassium phosphate and sodium bicarbonate, as well as organic salts such as sodium citrate, potassium citrate and sodium acetate.

The agent for treating diabetes of the present invention may be administered in a dosage form of injections (e.g., subcutaneous, intracutaneous, intramuscular, intravenous or intraperitoneal injections), in any dosage form suitable for transdermal, transmucosal or transnasal administration or in any dosage form suitable for oral administration (e.g., tablets, capsules, granules, solutions, suspensions). The present invention is not limited by the route of administration or dosage form, etc.

In the agent for treating diabetes of the present invention which comprises a stem cell-recruiting factor or factors as an active ingredient(s), the dose and frequency of its administration can be determined as appropriate by those skilled in the art by taking into account symptoms of a diseased patient to be treated. In general, the stem cell-recruiting factor(s) may be administered at a dose of 0.1 to 500 µg/kg/day per adult, preferably 1 to 50 µg/kg/day per adult, for 1 to 7 days per week. However, the present invention is not limited by the dose of the stem cell-recruiting factor(s).

After the agent for treating diabetes of the present invention is administered to increase the number of stem cells in the bone marrow and the peripheral blood, the cells can be collected and differentiated into β-cells in vitro. The β-cells thus differentiated may be returned to the body for use in treatment.

Since human G-CSF is already clinically used, e.g., as a therapeutic agent for neutropenia, the administration of human G-CSF is particularly preferred for recruiting stem cells into the peripheral blood to replenish disrupted pancreatic β-cells.

In the case of administering β-cell-regenerating factors other than stem cell-recruiting factors, these factors can be expected to produce an increased therapeutic effect when co-administered with a stem cell-recruiting factor(s). Treatment of diabetes using a stem cell-recruiting factor(s) can also be expected to increase its therapeutic effect when combined with administration of a drug currently used for diabetes (e.g., SU drugs, biguanide drugs and thiazolysine derivative drugs). Moreover, it is also possible to simultaneously administer a plurality of stem cell-recruiting factors. Alternatively, such treatment may be used in combination with gene therapy or the agent for treating diabetes of the present invention itself may be adapted to gene therapy by using a gene encoding a stem cell-recruiting factor.

Figure 2:
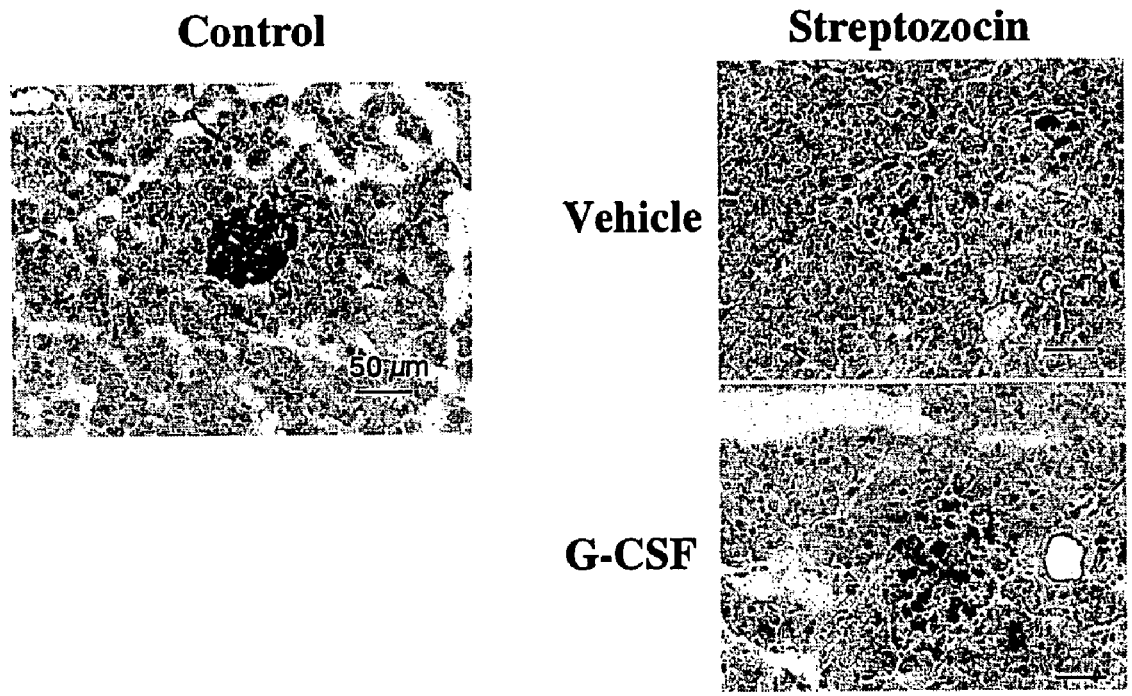
FIG. 2 shows pancreatic Langerhans β-cells immunostained with an anti-insulin antibody. The left panel shows normal mouse tissue, the upper right panel shows the mouse tissue administered with a vehicle after streptozocin administration, and the lower right panel shows the mouse tissue administered with G-CSF after streptozocin administration.

As shown in Example 1 and FIG. 2, pancreatic β-cells were disrupted in diabetic model mice, but the presence of β-cells was confirmed to some extent when G-CSF was administered to the mice. Thus, the agent for treating diabetes of the present invention is also effective as an agent for preventing β-cell disruption in pancreatic Langerhans' islets or an agent for regenerating β-cells in pancreatic Langerhans' islets.

The present invention further relates to a method for producing pancreatic Langerhans β-cells, which is characterized by collecting stem cells after administering a stem cell-recruiting factor or factors, and then differentiating the collected stem cells into pancreatic Langerhans β-cells.

Stem cells may be collected in a known manner, for example, by isolating mononuclear cells from the peripheral blood or by sorting blood having a stem cell marker such as CD34, c-kit or CD133 to give a stem cell fraction.

The stem cells thus collected may be differentiated into pancreatic Langerhans β-cells in any manner, for example, by culturing the stem cells in the presence of a differentiation-inducing factor for pancreatic Langerhans β-cells, by treating the stem cells with a differentiation-inducing factor for pancreatic Langerhans β-cells, or by growing the stem cells using cell fusion techniques.

The differentiation factor for pancreatic Langerhans β-cells used in the present invention is not limited in any way as long as it allows differentiation of stem cells into pancreatic Langerhans β-cells. Specific examples of such a factor include bFGF, Reg gene, TGF, IGF1, activin A, NGF, VEGF and interferons.

The method of the present invention is believed to be superior also from an ethical point of view because the present method allows the differentiation of autologous bone marrow cells into β-cells and is less likely to cause rejection reactions in patients compared with the current treatment of β-cell transplantation using embryonic stem cells. Moreover, the method of the present invention can be a radical treatment and can free diabetic patients from having to administer insulin injections, thus enabling significant improvements in the quality of life.

EXAMPLES

The present invention will be illustrated by way of the following experimental example.

Experimental Example 1

Streptozocin was intraperitoneally administered to mice at a dose of 100 mg/kg to disrupt their pancreatic cells, thereby creating diabetic models. Starting 1 day after streptozocin administration, G-CSF (300 µg/kg) or its vehicle was subcutaneously administered once a day for 9 consecutive days. Before and after 1, 2, 4, 7, 14 and 22 days of streptozocin administration, the blood glucose concentration was measured for each mouse. The results obtained are shown in FIG. 1. In the mice administered with streptozocin, the blood glucose concentration started to increase after streptozocin administration, but the G-CSF group showed a lower blood glucose concentration than the vehicle group.

Further, in a similar experiment, streptozocin was intraperitoneally administered to mice at a dose of 160 mg/kg, followed by subcutaneous administration of G-CSF (300 µg/kg) or its vehicle once a day for 8 consecutive days, starting from the day following the streptozocin administration. At two weeks after streptozocin administration, pancreases of the mice were extracted to prepare frozen sections. These sections were immunostained with an anti-insulin antibody to stain β-cells of pancreatic Langerhans' islets and provided for comparison with normal mouse pancreas. The results obtained are shown in FIG. 2. In the vehicle group, β-cells were disrupted by administration of streptozocin (upper right panel), whereas the presence of β-cells was confirmed to some extent in the G-CSF group (lower right panel). This is because G-CSF administration reduces the streptozocin-induced disruption of β-cells in pancreatic Langerhans' islets or regenerates the disrupted β-cells.

INDUSTRIAL APPLICABILITY

The present invention can be expected to provide a radical treatment for diabetes and enables significant improvements in the quality of a patient's life. The treatment according to the present invention is simple, safe and effective when compared to conventional treatment.

The invention claimed is:

1. A method for preventing β-cell disruption in pancreatic Langerhans' islets of a type II diabetes patient, which method comprises administering granulocyte colony-stimulating factor as an active ingredient of a composition to a type II diabetic patient in need thereof in an amount sufficient to provide said preventing.

2. The method of claim 1 wherein the granulocyte colony stimulating factor is administered without any other agent for preventing β-cell disruption in pancreatic Langerhans' islets.

* * * * *